United States Patent
Den Tandt et al.

(10) Patent No.: US 6,767,865 B2
(45) Date of Patent: Jul. 27, 2004

(54) AGROCHEMICAL SUSPENSION FORMULATIONS

(75) Inventors: Youry Den Tandt, Sint-Amands (BE); Johan Camiel Gabrielle, Kortenberg (BE)

(73) Assignee: Imperial Chemical Industries PLC, London (GB)

(*) Notice: Subject to any disclaimer, the term of this patent is extended or adjusted under 35 U.S.C. 154(b) by 8 days.

(21) Appl. No.: 10/304,063

(22) Filed: Nov. 26, 2002

(65) Prior Publication Data

US 2003/0161856 A1 Aug. 28, 2003

Related U.S. Application Data

(63) Continuation of application No. PCT/GB01/02367, filed on May 25, 2001.
(60) Provisional application No. 60/208,549, filed on Jun. 1, 2000.

(30) Foreign Application Priority Data

May 26, 2000 (GB) .............................................. 0012775

(51) Int. Cl.[7] .............................................. A01N 25/30
(52) U.S. Cl. ...................................... 504/362; 514/937
(58) Field of Search ........................... 504/362; 514/937

(56) References Cited

U.S. PATENT DOCUMENTS 5,089,259 A  2/1992  Wessling et al. ............. 424/497
5,321,049 A * 6/1994  Smith et al. ............. 514/772.6
5,508,035 A  4/1996  Wessling et al. ............. 424/405

FOREIGN PATENT DOCUMENTS

| DE | 3304457 A1 | 10/1983 |
|---|---|---|
| EP | 0007731 A2 | 2/1980 |
| EP | 0644205 A1 | 3/1995 |
| EP | 0739959 A1 | 10/1996 |
| WO | WO95/07614 | 3/1995 |
| WO | WO96/00251 | 1/1996 |
| WO | WO99/18787 | 4/1999 |
| WO | WO00/60942 | 10/2000 |

* cited by examiner

*Primary Examiner*—S. Mark Clardy
(74) *Attorney, Agent, or Firm*—Pillsbury Winthrop LLP

(57) ABSTRACT

Agrochemical suspension concentrates, particularly in aqueous or liquid oil based medium, comprise solid particles including one or more agrochemical active components; and a dispersing agent including a water soluble or dispersible styrene (meth)acrylic acid copolymer. In particular the styrene (meth)acrylic acid copolymer has a molar ratio of residues of (meth)acrylic acid monomer(s) to styrene monomer(s) from 20:1 to 1:5, particularly from 3:1 to 1:1. The formulation will usually also contain wetting agents; and/or adjuvants. The agochemical active can be plant growth regulators, herbicides, and/or pesticides, for example insecticides, fungicides, acaricides, nematocides, miticides, rodenticides, bactericides, molluscicides and bird repellants. The suspension formulations will typically be used diluted in water and sprayed onto plants or the soil surrounding the plants.

13 Claims, No Drawings

AGROCHEMICAL SUSPENSION FORMULATIONS

CROSS REFERENCE TO RELATED APPLICATIONS

This application is a continuation of International Application No. PCT/GB01/02367, filed May 25, 2001, and further claims benefit from U.S. Provisional Application No. 60/208,549, filed Jun. 1, 2000. These applications, in their entirety, are incorporated herein by reference.

This invention relates to agrochemical formulations and in particular to such formulations in the form of suspensions of solids including agrochemical active material in a liquid medium, particularly as suspension concentrates which are dispersible in water to give agrochemical suspensions, and to methods of treating plants by spraying them with such agrochemical suspensions, particularly diluted suspension concentrate formulations.

Agrochemical formulations are commonly applied by spraying, usually as a water based spray formulation. One formulation type is a suspension of solid particles including an agrochemical active (usually a water insoluble active) in a liquid medium, commonly initially formulated as a concentrate (a suspension concentrate) which is diluted before use as a spray. Dispersing agents, such as salts of naphthalene sulphonate formaldehyde condensates, lignosulfonates, maleic anhydride copolymers and condensed phenolsulphonic acids, and non-ionic dispersants such as EO/PO block copolymers, are commonly included in agrochemical suspensions and suspension concentrates to help disperse the active ingredient in the medium, particularly in concentrates, and improve the suspension and dispersion of the solid agrochemical in the dilute spray formulation.

The present invention is generally directed to agrochemicals in the form of water dilutable suspensions, particularly suspension concentrates, including styrene (meth)acrylic copolymers as dispersing agents for the agrochemical in the suspension concentrate and on mixing with water and in particular can provide good dispersion and suspension properties even after extended storage (ageing) of the suspension concentrate.

The present invention accordingly provides an agrochemical formulation, which is dilutable in water, in the form of a suspension, particularly in an aqueous liquid or a liquid oil based medium, of solid particles including one or more agrochemical active components; and a dispersing agent including a water soluble or dispersible styrene (meth) acrylic acid copolymer.

The present invention includes such an agrochemical formulation which further includes:

1 one or more wetting agents; and/or
2 one or more adjuvants;

The invention includes a method of making a spray mix in which an agrochemical suspension concentrate formulation of the invention is dispersed in water. The invention further includes a method of treating plants in which the plants or the soil surrounding the plants are sprayed with a spray mix made by mixing an agrochemical suspension concentrate formulation of the invention with water.

The agrochemical formulations of and used in the invention particularly take the form of dilutable concentrates which are typically diluted with water to form a suspension (dispersion) of an agrochemical when diluted in water before use, and specifically the invention includes:

a an agrochemical suspension concentrate, in which at least one agrochemical is dispersed in an aqueous carrier fluid, which further includes as a dispersing agent including a water dispersible styrene (meth)acrylic copolymer, and desirably further includes at least one adjuvant surfactant;

b an agrochemical suspension concentrate, in which at least one agrochemical is dispersed in a non-aqueous carrier fluid, which further includes as a dispersing agent including a water dispersible styrene (meth)acrylic copolymer, and desirably further includes at least one adjuvant surfactant;

c an agrochemical suspension concentrate including an agrochemical in microencapsulated form suspended in a carrier fluid which includes as a dispersing agent including a water dispersible styrene (meth)acrylic copolymer, and desirably further includes at least one adjuvant surfactant;

d an agrochemical suspoemulsion concentrate (commonly in the art simply referred to as a "suspoemulsion") including an agrochemical in water for use, in which solid particles including at least one agrochemical are dispersed in a carrier fluid which includes as a dispersing agent at least one water dispersible styrene (meth)acrylic copolymer, which further includes in solution or dispersion at least one emulsifier and at least one dispersant surfactant and desirably includes at least one adjuvant surfactant;

The water dispersible styrene (meth)acrylic copolymer used in this invention is for convenience sometimes referred to below as a polymeric dispersant. The polymeric dispersant is a styrene (meth)acrylic acid copolymer. The repeating units in the copolymer are conveniently considered as residues of monomer components.

The (meth)acrylic acid monomer(s) can be acrylic acid, methacrylic acid, crotonic acid or a mixture of two or more of these. The (meth)acrylic acid monomer(s) can be or include (meth)acrylic monomers which are derivatives of (meth)acrylic acid which include strong acid, especially sulphate acid or sulphonic acid groups (or their salts). Examples of such monomers include acrylamido methyl propyl sulphonate (AMPS) and (meth)acrylic acid isethionate. When present such strong acid modified monomers usually form from 1 to 30 mole %, more usually 2 to 20 mole %, and desirably from 5 to 15 mole %, of the acrylic acid monomers in the copolymer.

The styrene monomer(s) can be, and desirably is, styrene as such or a substituted styrene particularly a hydrocarbyl, desirably alkyl, substituted styrene, in which the substituent (s) are on the vinyl group or on the aromatic ring of the styrene e.g. α-methyl styrene and vinyl toluene. As with the (meth)acrylic acid monomer, the styrene monomer can be or include styrene monomers including strongly acid, particularly sulphonic acid substituents. When present such strong acid modified monomers usually form from 1 to 30 mole %, more usually 2 to 20 mole %, and desirably from 5 to 15 mole %, of the styrene monomers in the copolymer.

In the water dispersible styrene (meth)acrylic copolymer used in the invention, the molar ratio of residues of the (meth)acrylic acid monomer(s) to those of the styrene monomer(s) is generally from 20:1 to 1:5, more usually 10:1 to 1:2 and particularly from 3:1 to 1:1. Generally correspondingly, the proportions of residues of the monomers by weight are typically from 93 to 10%, more usually 87 to 25%, particularly 67 to 40%, of the (meth)acrylic acid monomer(s) and from 7 to 90%, more usually 13 to 75%, particularly 33 to 60%, of the styrene monomer(s).

Other monomers, such as acidic monomers e.g. itaconic acid or maleic acid or anhydride; strongly acidic monomers such as methallyl sulphonic acid (or a salt); or non-acidic acrylic monomers e.g. acrylic esters which may be alkyl esters particularly $C_1$ to $C_6$ alkyl esters such as methyl methacrylate, butyl methacrylate or butyl acrylate or hydroxy alkyl esters particularly $C_1$ to $C_6$ hydroxyalkyl esters such as hydroxy ethyl methacrylate, or hydroxy propyl methacrylate; or vinyl monomers such as vinyl acetate, can be included. Typically, the proportion of such other monomer(s) will be not more than about 25 mole %, usually not more than about 16 mole %, more usually not more than about 5 mole %, of the total monomers used. The proportion by weight of other monomers will typically be not more than about 30%, usually not more than about 20%, more usually not more than about 10%.

The polymeric dispersant can be a single styrene acrylic acid copolymer or a blend including two or more such copolymers. In particular, when strong acid residues are included in the polymeric dispersant, the dispersant can be a blend of copolymer including strong acid residues and copolymer not including such residues. In such blends, it is generally desirable that the ratio of such copolymers is from 1:10 to 10:1, more usually 5:1 to 1:5, by weight. In particular, the proportion of copolymer including strong acid residues is desirably at least 25%, more usually at least 40%, by weight of the polymeric dispersant.

When strong acid residues are included in the polymeric dispersant, the overall proportion of monomer residues including strong acid groups is desirably from 0.25 to 25 mole %, more usually from 0.5 to 20 mole % and desirably from 1 to 10 mole %.

The inclusion of monomers having strongly acidic substituent groups in the polymeric dispersant can provide improved dispersion of the solid components of the agrochemical formulations when diluted in hard water, particularly water having a hardness above 500 ppm e.g. up to 1000 ppm, up to 2000 ppm or even up to 5000 ppm.

The polymeric dispersant desirably has a molecular weight of from 750 to 50000 more usually not more than about 20000, more desirably from 1000 to 10000 and particularly from 1500 to 5000. The polymeric dispersant can be used as the free acid or as a salt. In practice, the form present in a formulation will be determined by the acidity of the formulation. Desirably, the formulation will be near neutral and so most of the acid groups will be present as salts. The cations in any such salt can be alkali metal, particularly sodium and/or potassium, ammonium, or amine, including alkanolamine such as ethanolamine, particularly tri-ethanolamine. Polymeric dispersants used in this invention are desirably free from solvent which might interfere with the active ingredient or cause the granules to stick together. Further desirably the polymeric dispersant is heat stable and non gelling.

The polymeric dispersants can be made by free radical initiated polymerisation, e.g. using a peroxide or a redox initiator, particularly by solution polymerisation, of the constituent monomers, optionally also with a chain transfer agent such as an alkyl mercaptan which acts to control the molecular weight of the polymer. Suitable methods are described for example in EP 0697422 A.

To aid dispersion of the active component(s) in the spray formulation after dilution with water, it is desirable that the polymeric dispersant is compatible with and more usually interacts strongly with, the surface of any water insoluble material containing active agrochemical present in the formulation. Water insoluble agrochemical actives may be used as powders, absorbed/adsorbed onto solid support material or, particularly for liquid actives, in microencapsulated form. Desirably when microencapsulated actives are used the polymeric dispersant is also desirably compatible with common shell wall materials used in such microcapsules e.g. polyurea, polyurethane, polyester, polyearbonate, polysulfonamide and polyamide including proteins such as gelatin.

The dispersing agent used in the formulation of the invention may be wholly of styrene (meth)acrylic copolymers or it may include other dispersant materials such as the conventional dispersants mentioned above, such as naphthalene sulphonate formaldehyde condensates, lignosulfonates, maleic anhydride copolymers and condensed phenolsulphonic acid and their salts. When used in such combinations the weight ratio of styrene (meth)acrylic copolymer(s) to such conventional dispersants will usually be at least 1:5 and more usually from 1:4 to 10:1, particularly from 1:2 to 5:1.

Other conventional dispersants and dispersing aids such as polyvinylpyrrolidone (PVP), polyvinyl alcohol (PVOH), phosphate esters such as the tristeryl phenol based phosphate esters available as Soprofor FL, carbomethoxycellulose (CMC), starch, alginate, gum arabic, sorbitol, and sucrose (as mentioned above) can be included. When used such conventional materials are typically used as minor components of the dispersing agent e.g. at from 1 to 20% by weight of the total dispersant.

The agrochemical active material can be one or more of a wide range of water dispersible agrochemically active materials. Description of the actives as water dispersible means that they can be dispersed in water, if necessary with the use of dispersing agents and includes water dispersible solid forms of active agrochemicals that may not themselves be dispersible in water e.g. with the agrochemical absorbed in or adsorbed onto a support or as a (micro)encapsulated liquid or solution. Specifically, the active may be one or more plant growth regulators, herbicides, and/or pesticides, for example insecticides, fungicides, acaricides, nematocides, miticides, rodenticides, bactericides, molluscicides and bird repellants. Usually, the active will be a water insoluble or immiscible material. Specific examples of actives include:

Herbicides: including triazines such as Atrazine{6-chloro-N-ethyl-N'-(1-methylethyl)-1,3,5-triazine-2,4-diamine, and Prometryn{N,N'-bis(1-methylethyl)-6-(methylthio)-1,3,5-triazine)-2,4-diamine}, substituted ureas such as Diuron{N'-(3,4-dichlorophenyl)-N,N-dimethylurea}, sulphonyl ureas such as metsulfuron-methyl{2-[[[[(4-methoxy-6-methyl-1,3,5-triazin-2-yl) amino]carbonyl]amino]sulfonyl]benzoate}, triasulfuron{2-(2-chloroethoxy)-N-[[(4-methoxy-6-methyl-1,3,5-triazin-2-yl) amino]carbonyl]benzenesulfonamide}, tribenuron-methyl{methyl 2-[[[[(4-methoxy-6-methyl-1,3,5-triazin-2-yl)methylamino]carbonyl]amino]sulfonyl]benzoate} and chlorsulfuron{2-chloro-N-[[(4-methoxy-6-methyl-1,3,5-triazin-2-yl)amino]carbonyl]benzenesulfonamide}, bis-carbamates such as Phenmedipham{3-[(methoxycarbonyl)amino]phenyl(3-methylphenyl) carbamate};

Fungicides: including thiocarbamates, particularly alkylenebis(dithiocarbamate)s, such as Maneb{[1,2-ethanediylbis-[carbamodithiato](2-)]manganese} and Mancozeb{[[1,2-ethanediyl-bis[carbamodithiato]](2-)] manganese mixture with [[1,2-ethanediylbis [carbamodithiato]](2-)]zinc}, strobilurins such as azoxystrobin{methyl(E)-2-[[6-(2-cyanophenoxy)-4- pyrimidinyl]oxy]-a-(methoxymethylene)benzeneacetate} and kresoxim-methyl{(E)-a-(methoxyimino)-2-[(2-methylphenoxy)methyl]benzeneacetic acid methyl ester}, dicarboximides such as iprodione{3-(3,5-dichlorophenyl)-N-isopropyl-2,4-dioxo imidazolidine-1-carboxamide}; azoles such as propiconazole{1-[2-(2,4-dichloro-phenyl)-4-propyl-1,3-dioxolan-2-yl-methyl-1H-1,2,4-triazole}, and tebuconazole{(RS)-1-p-chlorophenyl-4,4-dimethyl-3-(1H-1,2,4-triazole-1-ylmethyl)-pentan-3-ol}; halophthalonitriles such as chlorothalonil{2,4,5,6-tetrachloro-1,3-dicyanobenzene}; and inorganic fungicides such as Copper hydroxide{Cu (OH)$_2$};

Insecticides: including benzoyl ureas such as Diflubenzuron{N-[[(4-chlorophenyl)amino]carbonyl]-2, 6-difluorobenzamide)}; and carbamates such as carbaryl{1-naphthyl methylcarbamate};

Acaricides including: tetrazines such as Clofentezine{3,6-bis(2-chlorophenyl)-1,2,4,5-tetrazine}.

The suspension formulations can include solid support, filler or diluent material(s) which is desirably inert to the agrochemically active material, but which is readily dispersible in water, if necessary in conjunction with dispersing agents. They can be used to adjust the viscosity of the concentrate or the dilute spray formulation and/or as a support for the active. Examples include clays such as kaolin (china clay) and bentonite clays, which may be natural bentonites or modified e.g. activated bentonites, synthetic and diatomaceous silicas, calcium and magnesium silicates, titanium dioxide, aluminium, calcium or magnesium carbonate, ammonium, sodium, potassium, calcium or barium sulphate, charcoal, starch, including modified starches such as alkyl and carboxyalkyl starches, cellulose, such as microcrystalline cellulose, and cellulose derivatives such as carboxyalkyl cellulose, and mixtures of two or more such solid support, filler, diluent materials.

A further possible way of incorporating agrochemical active materials in formulations of and used in this invention is as liquids or solutions of the active in a suitable, usually water immiscible, solvent in which are microencapsulated. The water immiscible liquid which is or includes at least one compound of the formula (I) can be or be part of the fluid within which the microcapsules are dispersed and/or it may act as the solvent (when used) for the active within the microcapsules. The microcapsules can be made by conventional methods from an emulsion of the liquid or dissolved active in a, normally aqueous, liquid for example by coacervation, particularly using proteinaceous polymers such as gelatin, in situ polymerisation of e.g. urea and/or melamine formaldehyde polymers, to form the capsule walls, or by interfacial polymerisation. Once microencapsulated, the active is within the bulk of the formulation in substance present as a dispersion and can be formulated as described below.

The particle size of the particles of or including active agrochemical in an agrochemical suspension should be small enough that there is no practical risk of blocking spray jets. Typically, as mixed into formulations during make up the average particle size of solid agrochemicals is from 50 to 100 $\mu$m, but formulations are typically wet milled after mixing to reduce the average particle size to from 1 to 10, particularly 1 to 5, $\mu$m. Agrochemicals adsorbed on or absorbed in solid supports will in effect have the particle size of the support, which is desirably from 1 to 5 $\mu$m. The average particle size of microcapsules of encapsulated agrochemicals will usually be from 1 to 10 $\mu$m, more usually from 5 to 10 $\mu$m. The use of dispersants is in part to avoid agglomeration of the particles of or including agrochemicals during storage and use.

The agrochemical formulation can include adjuvants, particularly surfactant adjuvants, especially non-ionic surfactants, such as alcohol alkoxylates e.g. ethoxylates, particularly of $C_8$ to $C_{18}$ alcohols which can be linear, branched or linear/branched mixtures; alkylamine alkoxylates e.g. ethoxylates, particularly of $C_8$ to $C_{18}$ alkylamines; sorbitol and sorbitan fatty acid, particularly $C_8$ to $C_{18}$ fatty acid, esters and their ethoxylated derivatives; and alkyl, particularly $C_6$ to $C_{14}$ alkyl, polysaccharides. For example, typical weight ratios of adjuvant to agrochemical active range from 1:3 to 10:1. The adjuvant can be included in the formulation as such or adsorbed in or adsorbed on a solid support e.g. silica or diatomaceous earth, which can be solid support, filler or diluent material as mentioned above, or by including it as a clathrate especially a urea clathrate.

Other surfactants can be included particularly as wetting agents to speed up dispersion of the concentrate in water to form the spray or to enhance the wetting of plant leaves by the spray. Examples of wetting agents include nonionic surfactants such as alcohol ethoxylates e.g. $C_9$ to $C_{15}$, particularly primary, alcohols, which may be linear or branched, particularly mono-branched, ethoxylates with from 5 to 30 moles of ethylene oxide; and alkoxylates of such alcohols particularly mixed ethoxylate/propoxylates which may be block or random mixed alkoxylates, typically containing from 3 to 10 ethylene oxide residues and from 1 to 5 propylene oxide residues, particularly where the polyalkoxylate chain is terminated with propylene oxide unit(s); polyoxyethylene/polyoxypropylene copolymers, particularly block copolymers, such as the Synperonic PE series of copolymers and Atlas G 5000 available from Uniqema, and alkyl polysaccharides; anionic surfactants e.g. isethionates, such as sodium cocoyl isethionate, naphthalene sulphonic acids or sulphosuccinates. Mixtures of such wetting agents can also be used.

Blends of the polymeric dispersant(s) with other dispersants e.g. conventional dispersants such as salts of naphthalene sulphonate formaldehyde condensates, lignosulfonates, maleic anhydride copolymers and condensed phenolsulphonic acids, and non-ionic dispersants such as EO/PO block copolymers may be used if desired. In such blends the polymeric dispersant is desirably at least 25%, more usually at least 50% and desirably at least 75%, and correspondingly, the other dispersants, when used, typically form from 1 to 75%, more usually 2 to 50% and desirable 5 to 25%, by weight of the total dispersant.

The total amount of dispersing agent used in the suspensions of this invention is typically from 3 to 10%, particularly from 5 to 8%, by weight of the suspension concentrate. The amount of polymeric dispersant used is desirably at least 1% and more usually 2 to 10%, particularly from 5 to 8% by weight of the total suspension concentrate formulation.

When wetting agents are used the amount used is typically from 1 to 5%, particularly 2 to 4%, by weight of the suspension concentrate and the weight ratio of dispersing agent to wetting agent is typically from 1:1 to 1:10, desirably from 2:1 to 4:1. Generally, the combined amount of dispersing agent and wetting agent is from 3 to 10%, more usually 5 to 8% by weight of the total suspension concentrate formulation.

The total amount of agrochemically active material will typically be from 10 to 95%, more particularly 20 to 90% by weight of the suspension concentrate. When the suspension concentrate does not include an adjuvant, the amount of agrochemically active material will typically be from 40 to 95%, more particularly 50 to 90% by weight of the suspension concentrate. When an adjuvant is included the amount of agrochemically active material will typically be from 10 to 70%, more particularly 20 to 50% by weight of the suspension concentrate and the amount of adjuvant from 10 to 50%, particularly 20 to 40%, by weight of the total suspension concentrate. Typically the amount of adjuvant is from 1 to 10, more usually from 1 to 5, parts by weight per part by weight of active. The combined proportion of agrochemically active material and adjuvant is typically from 10 to 95%, more particularly 20 to 90% by weight of the suspension concentrate.

The amount of solid support, when used, is typically from 0.05 to 2, particularly 0.1 to 1, parts by weight per part by weight of the combination of agrochemical active, adjuvant (when used), dispersing agent and wetting agent (when used). Thus, the amount of solid support material used is typically from 0 to 70%, particularly 5 to 50%, by weight of the suspension concentrate.

The amounts of the major components of the suspension formulations of the invention are desirably within the ranges indicated in the following table:

| Component | Amount (% w/w on suspension concentrate) | |
| --- | --- | --- |
| | broad | preferred |
| agrochemical active | 10 to 95 | 20 to 90 |
| without adjuvant | 40 to 95 | 50 to 90 |
| with adjuvant | 10 to 70 | 20 to 50 |
| adjuvant (when present) | 10 to 50 | 20 to 40 |
| dispersing agent | 3 to 10 | 5 to 8 |
| polymeric dispersant | 1 to 10 | 3 to 8 |
| wetting agent (when present) | 1 to 5 | 2 to 4 |
| dispersing + wetting agents | 3 to 10 | 5 to 8 |
| ratio dispersant: wetter | 1:1 to 10:1 | 2:1 to 4:1 |
| solid support (when present) | 0 to 50 | |
| medium | to 100 | |

Water based suspension concentrates are generally used to disperse water insoluble active ingredients dispersed directly in the aqueous phase or absorbed in or adsorbed onto a solid support or as microencapsulated liquid or solutions of actives. In the invention such formulations also include polymeric dispersant and may include other dispersant surfactants. Desirably the formulations also include adjuvants. In general, on dilution into water the solid including active generally becomes dispersed directly in the water. Overall the composition of water based suspension concentrates is typically as set out below:

| | amount (wt %) | |
| --- | --- | --- |
| material | typical | desirable |
| agrochemical active | 5 to 75 | 10 to 50 |
| dispersant | 1 to 20 | 3 to 10 |
| polymeric dispersant | 1 to 10 | 3 to 7 |
| dispersant surfactant (when used) | 1 to 10 | 3 to 7 |
| wetter | 1 to 5 | 2 to 4 |
| adjuvant (when used) | 1 to 50 | 3 to 20 |
| water | to 100 | |

Oil based suspension concentrates are used to disperse oil insoluble active ingredients which are also water insoluble or are too water soluble to include in a water based flowable suspension concentrate or are not chemically stable in water. In the invention such formulations also include polymeric dispersant and may include dispersants, particularly condensed fatty acid surfactants, and also usually include emulsifier(s) for the carrier fluid phase on dilution into water. Such formulations desirably also include adjuvants. On dilution into water a water insoluble solid active may become dispersed directly in water or may be a solid dispersed phase in the emulsified oil phase (this is very similar to suspoemulsions on dilution see also below). Overall typical compositions of oil based concentrates are set out below:

| | amount (wt %) | |
| --- | --- | --- |
| material | typical | desirable |
| oil insoluble agrochemical active | 5 to 75 | 10 to 50 |
| carrier fluid | 10 to 94 | 30 to 81 |
| dispersant | 1 to 20 | 3 to 10 |
| emulsifier surfactant (when used) | 1 to 20 | 3 to 10 |
| adjuvant | 0 to 20 | 3 to 10 |

Agrochemical suspoemulsion concentrates are formulations which on dilution (in water) give suspoemulsions i.e. which include at least one liquid (emulsion) disperse phase and at least one solid disperse phase, in a continuous aqueous phase. The concentrate formulation can itself be a suspoemulsion, in effect just more concentrated (having less water) than the diluted (spray) formulation; or it may be a dispersion of a solid disperse phase in an emulsifyable concentrate, which on dilution forms an emulsion. They are particularly suitable for agrochemical formulations which include an oil soluble active, present as a solution in the oil emulsion disperse phase, and a solid water insoluble (and usually also oil insoluble) active, i.e. the solid components usually include an agrochemical active, present as dispersed particles, although other formulation components may also be present as dispersed solid particles. The solid dispersed phase may be dispersed within the oil based emulsion droplets. Suspoemulsions are typically based on an oil solution of one agrochemical also including a solid water insoluble active or other solid component present as dispersed particles. They usually include surfactant(s) as emulsifiers, particularly oil in water emulsifiers, to stabilise the emulsion formed on dilution in water to normal spray concentration, and as dispersant for the solid particles in the oil phase and/or the aqueous phase. Suspoemulsion concentrates are typically diluted in water for spray application to form suspoemulsions. Overall the composition of suspoemulsion concentrates are typically as set out below:

| | amount (wt %) | |
| --- | --- | --- |
| material | typical | desirable |
| oil soluble agrochemical active | 0.1 to 50 | 10 to 40 |
| solid dispersed components | 0.1 to 50 | 10 to 40 |
| carrier fluid | 1 to 50 | 5 to 40 |
| dispersant | 1 to 20 | 2 to 10 |
| polymeric dispersant | 1 to 10 | 3 to 7 |
| dispersant surfactant (when used) | 1 to 10 | 3 to 7 |
| emulsifier | 1 to 20 | 4 to 7 |
| adjuvant (when used) | 1 to 50 | 3 to 20 |
| water | 10 to 80 | 20 to 60 |

Other materials that can be include in the suspension concentrates include:

antifreeze materials such as ethylene glycol or monopropylene glycol, typically at concentrations of 2 to 20%, desirably 5 to 15% and particularly at about 10% by weight of the concentrate formulation;

buffering materials e.g. so that the pH of the diluted material is desirably from 4 to 9, more usually from 5 to 8 and particularly about 7;

penetrating agents; antifoams; safeners such as Bitrex; pigments and/or dyes; anti-caking additives, particularly to discourage the formation of a caked precipitate if any solids do separate from the suspension; sequestrants; and adhesives.

The following Examples illustrate the invention. All parts and percentages are by weight unless otherwise stated.

Materials

Dispersants—styrene acrylic acid copolymers:

| Code | AA/Sty* | MW | |
|---|---|---|---|
| DS1 | 2:1 | 3800 | ca 40% by weight active material in water |
| DS2 | 2:1 | 3800 | 90% by weight active material (DS1 spray dried) |
| DS3 | 2:1 | 42000 | 20% by weight active material in water |
| DS4 | 2:1 | 3700 | anionically modified co-polymer** 40% active material in water |

*molar acrylic acid to styrene monomer ratio in copolymer
**the acrylic acid component includes a proportion of a sulphonated acrylic monomer Agrochemical Actives

| Code | Commercial name | Description |
|---|---|---|
| Act1 | Atrazine | 99% by weight active material ex Novartis (Ciba) |
| Act2 | Cu(OH)$_2$ | 100% active material ex Industrias Quimicas del Valles |
| Act3 | Diuron | 96 (min) % by weight active material in ex Sanachem |
| Act4 | simazine | 98% active material ex Syngenta |
| Act5 | iprodione | 95% active material ex Aventis |
| Act6 | atrazine | 97% active material ex Dow |
| Act7 | carbaryl | 97.5% active material ex Aventis |

Other Materials

| | | |
|---|---|---|
| 342 water | | 342 ppm hardness WHO standard hard water |
| 1000 water | | 1000 ppm hardness water |
| MPG | | mono propylene glycol |
| Surf1 | Atlox 4894 | alcohol alkoxylate surfactant blend ex Uniqema |
| Surf2 | Atlox MBA 13/8 | alcohol alkoxylate surfactant ex Uniqema |
| Surf2 | Atlas G5000 | Polyalkylene glycol ether ex Uniqema |
| Surf2 | Synperonic A7 | POE (7) synthetic primary C13/15 alcohol ex Uniqema |
| Th1 | Kelzan | xanthan gum thickener ex Kelco |

Test Methods

Dispersibility (%)—is a measure of the stability of the dispersed solids in water—was assessed by dispersing 3 g of the granular formulation in 100 ml of 342 water in a test cylinder. The cylinder was inverted 30 times and allowed to stand for 30 minutes. The upper 90% were drawn off with a suction tube, taking care not to disturb the sediment. The remaining liquid and any sediment were transferred to an evaporating dish and dried in an oven at 50° C. to constant weight. The resulting powder was weighed (y g). The dispersibility (%) is the concentration of the powder in the upper 90% of the water expressed as:

[111.(3−y)/3]%[equivalent to 33.(3−y)%]

Physical suspension (PS) is a measure of the resistance of a diluted concentrate formulation to produce sediment. It was evaluated as the depth in mm of sediment in a 100 ml Nessler tube containing a sample of concentrate diluted 19:1 with 342 and 1000 water after 1 and 4 hours.

Ageing:—The effect of ageing on the samples of the suspension concentrate was assessed by storing the concentrate at ambient temperature or in an oven at 50° C. The dispersibility of the formulations was assessed fresh (0) and reassessed after storage for periods of time from e.g. 1 week (1W), 10 days (10D), or 1 month (1M).

Viscosity—(Visc. in mPa.s) was measured on a Brookfield RVT viscometer using a no 4 spindle at 5 rpm (ca 0.083 Hz).

EXAMPLE 1

A water based suspension concentrate, using Atrazine as the agrochemical active, was made up by mixing the components (except the dispersant) and milling. After milling the dispersant was added. The amounts of material used and the results of dispersibility testing of the concentrate fresh and after storage are indicated in Table 1 below.

TABLE 1

| | Formulation | | | | | Dispersion (%) | |
|---|---|---|---|---|---|---|---|
| | Act1 | MPG | Surf1 | Dispersant | | | |
| Ex No | (g) | (g) | (g) | type | (g) | Water | 0 | 1W40 |
| 1.1 | 500 | 100 | 20 | DS1 | 30 | to 1 l | 80 | 85 |
| 1.2 | | | | DS2 | | to 1 l | 80 | 85 |
| 1.3 | | | | DS3 | | to 1 l | 80 | 83 |

EXAMPLE 2

Water based suspension concentrates were made up using the general formulation:

| | |
|---|---|
| active ingredient | 500 g |
| DS3 | 50 g |
| Surf2 | 20 g |
| MPG | 100 g |
| water | balance to 1 liter |

The polymeric dispersant and surfactant were dissolved in the MPG and a portion of the water, the active ingredient was then added and the volume increased to 1 liter with water. The mixture was homogenised in a Silverson mixer and milled with in a Dyno Mill KDL. If necessary a few drops of silicone based antifoam were added to suppress foaming during homogenisation. The viscosity and dispersibility of the concentrates in 342 water and 1000 water were measured and the results are set out in Table 2 below.

TABLE 2

| | | Visc | Dipersibility (%) | |
|---|---|---|---|---|
| Ex No | Active | (mPa · s) | 342 water | 1000 water |
| 2.1 | Act2 | 150 | 96 | 93 |
| 2.2 | Act3 | 550 | 94 | 93 |

EXAMPLE 3

Suspension concentrate formulations were made up with various agrochemical active compounds and using dispersing agent DS4, an anionically modified acrylic acid styrene copolymer. Batches (300 g) of each formulation were made up using a Waring Blender adding the water first followed by the thickener which was predispersed in the MPG followed by the surfactants and dispersant and finally adding the agrochemical active (air-milled to a particle size less than 10 $\mu$m) under moderate agitation and mixing continued for a total of 10 minutes. The concentrates were formulated to contain 600 g.l$^{-1}$ active agrochemical. The formulations used are set out in Table 3a below. The results of testing are set out in table 3b below.

TABLE 3a

| Ex No | Active Type | (g) | Surf3 (g) | Surf4 (g) | DS4 (g) | Th1 (g) | MPG (g) | Water (g) |
|---|---|---|---|---|---|---|---|---|
| 3.1 | Act4 | 157.56 | 3.6 | 0.6 | 5.16 | 0.39 | 18 | 114.69 |
| 3.2 | Act5 | 160.29 | 3.6 | 1.8 | 1.74 | 0.39 | 18 | 114.18 |
| 3.3 | Act6 | 166.23 | 3.6 | 1.8 | 1.74 | 0.39 | 18 | 108.24 |
| 3.4 | Act7 | 165.24 | 3.6 | 1.8 | 1.74 | 0.39 | 18 | 109.23 |

TABLE 3b

| Ex No | Active | Visc. (mPa·s) | PS 342 water 1 hour | PS 342 water 4 hour | PS 1000 water 1 hour | PS 1000 water 4 hour |
|---|---|---|---|---|---|---|
| 3.1 | Act4 | 2840 | 2 | 3 | 2 | 3 |
| 3.2 | Act5 | 2960 | — | 2 | — | 1 |
| 3.3 | Act6 | 2440 | 1 | 2 | 1 | 2 |
| 3.4 | Act7 | 3160 | 1 | 5 | 2 | 7 |

What is claimed is:

1. An agrochemical suspension formulation, which is dilutable in water, in the form of a suspension of solid particles including of one or more agrochemical active components and a dispersing agent including a water dispersible styrene (meth)acrylic copolymer which comprises units of acrylic acid, methacrylic acid, crotonic acid or a mixture of two or more of these.

2. An agrochemical formulation as claimed in claim 1 which further includes at least one of:
  1) one or more wetting agents; and/or
  2) one or more adjuvants.

3. An agrochemical formulation as claimed in claim 1 wherein in the styrene (meth)acrylic copolymer the styrene monomer is styrene or an alkyl substituted styrene.

4. An agrochemical formulation as claimed in claim 1 wherein the styrene (meth)acrylic copolymer further comprises (meth)acrylic acid monomer residues including a strong acid group or salt thereof.

5. An agrochemical formulation as claimed in claim 1 wherein the styrene (meth)acrylic copolymer further comprises residues of monomers including a strong acid or salt thereof.

6. An agrochemical formulation as claimed in claim 1 wherein in the styrene (meth)acrylic copolymer the molar ratio of the residues of the (meth)acrylic acid monomer to those of the styrene monomer is from 10:1 to 1:2.

7. An agrochemical formulation as claimed in claim 1 wherein the styrene (meth)acrylic copolymer further comprises residues of one or more of itaconic acid, maleic acid or anhydride, acrylic alkyl esters, acrylic hydroxy alkyl esters, or vinyl acetate.

8. An agrochemical formulation as claimed in claim 7 wherein the styrene (meth)acrylic copolymer further comprises residues of one or more of methyl methacrylate, butyl (meth)acrylate, hydroxy ethyl methacrylate, or hydroxy propyl methacrylate.

9. An agrochemical formulation as claimed in claim 1 wherein the agrochemical active is one or more plant growth regulators, herbicides, and/or pesticides.

10. A method of making a spray mix in which an agrochemical formulation as claimed in claim 1 is dispersed in water.

11. A method of treating plants in which the plants or the soil surrounding the plants are sprayed with a spray mix made by dispersing an agrochemical formulation as claimed in claim 1 in water.

12. An agrochemical formulation as claimed in claim 4 wherein the (meth)acrylic acid monomer residues including a strong acid comprises residues of (meth)acrylic acid monomer having a sulphonic acid group or salt thereof.

13. An agrochemical formulation as claimed in claim 5, wherein the residues of monomers having a strong acid group comprise monomers having a sulphonic acid group or salt thereof.

* * * * *